United States Patent
Takahara

(10) Patent No.: US 9,810,648 B2
(45) Date of Patent: Nov. 7, 2017

(54) X-RAY FLUORESCENCE ANALYZER AND X-RAY FLUORESCENCE ANALYZING METHOD

(71) Applicant: HITACHI HIGH-TECH SCIENCE CORPORATION, Tokyo (JP)

(72) Inventor: Toshiyuki Takahara, Tokyo (JP)

(73) Assignee: HITACHI HIGH-TECH SCIENCE CORPORATION, Tokyo (JP)

( * ) Notice: Subject to any disclaimer, the term of this patent is extended or adjusted under 35 U.S.C. 154(b) by 0 days.

(21) Appl. No.: 14/948,297

(22) Filed: Nov. 21, 2015

(65) Prior Publication Data

US 2016/0146745 A1 May 26, 2016

(30) Foreign Application Priority Data

Nov. 26, 2014 (JP) .................. 2014-238669

(51) Int. Cl.
*G01N 23/223* (2006.01)
*H01J 35/16* (2006.01)

(52) U.S. Cl.
CPC ............ *G01N 23/223* (2013.01); *H01J 35/16* (2013.01); *G01N 2223/076* (2013.01)

(58) Field of Classification Search
CPC .......... G01N 23/223; G01N 2223/076; G01N 2223/301; G01N 23/2204
See application file for complete search history.

(56) References Cited

U.S. PATENT DOCUMENTS

2005/0045821 A1* 3/2005 Noji ..................... G01N 23/225
250/311
2007/0286341 A1 12/2007 Kamekawa et al.
2012/0235036 A1* 9/2012 Hatakeyama ...... G01N 23/2251
250/310
2013/0101085 A1 4/2013 Kita et al.
2013/0251100 A1* 9/2013 Sasaki .................. G01N 23/046
378/20
2015/0248991 A1* 9/2015 Ogawa .................... H01J 37/20
250/491.1

FOREIGN PATENT DOCUMENTS

JP 2000-171421 A 6/2000
JP 2001-281177 A 10/2001
JP 2002-005858 9/2002

OTHER PUBLICATIONS

Extended Search Report in corresponding European Application No. 15196104.2, dated Mar. 31, 2016, 7 pages.

* cited by examiner

*Primary Examiner* — Hoon Song
(74) *Attorney, Agent, or Firm* — Brinks Gilson & Lione

(57) ABSTRACT

An X-ray fluorescence analyzer includes: a sample stage; an X-ray source; a detector; an X stage; a Y stage; a θ stage; and a shielding container, wherein the irradiation position with primary X-rays is set at an offset position from a movement center of the X stage and the Y stage, wherein an irradiation area that is irradiatable with the primary X-rays is set to a selected segmented area from among segmented areas that are defined by segmenting the surface of the sample into four parts with a virtual segment lines in the X direction and the Y direction passing through the movement center, and wherein the θ stage is configured to switch the selected segmented area into any one of the segmented areas by rotating the sample stage by every 90 degrees.

8 Claims, 5 Drawing Sheets

X-RAY FLUORESCENCE ANALYZER AND X-RAY FLUORESCENCE ANALYZING METHOD

CROSS-REFERENCE TO RELATED APPLICATION

This application claims priority from Japanese Patent Application No. 2014-238669, filed on Nov. 26, 2014, the entire subject matter of which is incorporated herein by reference.

BACKGROUND

1. Field of the Invention

The present invention relates to an X-ray fluorescence analyzer that is capable of detecting toxic substances or the like and that is used for screening products or measuring a film thickness of plating or the like and an X-ray fluorescence analyzing method using the X-ray fluorescence analyzer.

2. Description of the Related Art

In a fluorescent X-ray analysis, a spectrum is acquired from energy by irradiating a sample with X-rays emitted from an X-ray source and detecting fluorescent X-rays which are characteristic X-rays emitted from the sample using an X-ray detector, and a qualitative analysis or a quantitative analysis of the sample or film thickness measurement of the sample is performed. Since samples can be rapidly analyzed in a non-destructive manner by the fluorescent X-ray analysis, the fluorescent X-ray analysis is widely used in the fields of process control, quality control, and the like. In recent years, high precision and high sensitivity of the fluorescent X-ray analysis have been achieved, and thus microdetermination is enabled. In particular, the fluorescent X-ray analysis is expected to become widespread as an analysis method of detecting toxic substances contained in materials, complex electronic parts, or the like.

For example, as illustrated in FIG. 5, an X-ray fluorescence analyzer according to the related art is provided with an X stage (not illustrated) that moves a sample stage 2 on which a sample S is mounted in the X direction, a Y stage (not illustrated) that moves the sample stage 2 in the Y direction, and an X-ray shielding enclosure 108 that accommodates the X stage and the Y stage therein so as to prevent or suppress exposure of an operator in measuring a sample. In this apparatus, it is necessary to ensure the size of the X-ray shielding enclosure 108 to be large enough to receive movable ranges of the X stage and the Y stage.

For example, JP-A-2002-005858 discloses a total-reflecting X-ray fluorescence analyzer provided with an X stage that moves a sample stage on which a disc-like sample is mounted in the X direction, a Y stage that moves the sample stage in the Y direction, and a θ stage that rotates the sample stage around a rotation axis perpendicular to the X stage and the Y stage. In this apparatus, for example, when a desired measurement part is present on the left side of the center of the sample and an irradiation position with primary X-rays is present on the right side, the desired measurement part is arranged at a position which is irradiated with primary X-rays by appropriately rotating the sample (for example, by 180 degrees) on a horizontal plane using the θ stage to position the desired measurement part on the right side of the center of the sample.

In the related art, the following problems may remain.

In the X-ray fluorescence analyzer according to the related art, particularly, when a large-area sample such as an electronic printed circuit board is measured, it is necessary to increase the movable ranges of the X stage and the Y stage so as to measure the entire surface of the sample. For example, as illustrated in FIG. 5, a wide movable range H1 corresponding to the area of the sample S is necessary, a sample stage movable range which is four times the sample area is necessary, the X-ray shielding enclosure 108 increases in size, an occupied area for installation of the apparatus increases, and thus there is a problem in that it is difficult to secure an installation location of the apparatus. Even when an installation location is secured, a sample input/output door of the apparatus increases in size and an opening and closing operation thereof imposes a burden on an operator. In order to solve this problem, means for reducing the occupied area of the apparatus by setting a measured head party in which an X-ray generating system or a detection system is disposed to be movable, but a moving mechanism of the measurement head increases in size and thus there is a problem in that apparatus costs increase and the measurement position is not stabilized.

In the conventional apparatus described in JP-A-2002-005858, since the θ stage is provided, a part which cannot be irradiated with primary X-rays only by the movements of the X stage and the Y stage is moved to an irradiation position with primary X-rays by rotating a disc-like sample. However, in this apparatus, a disc-like sample is merely rotated by 180 degrees to face the opposite side for the purpose of measuring the disc-like sample. Accordingly, when a large-area sample such as an electronic printed circuit board is measured, there is a problem in that the measurement cannot be efficiently performed. Particularly, when the X stage and the Y stage having a small movable range are employed to decrease the size of the apparatus, the entire surface of a sample cannot be efficiently measured only by properly rotating the θ stage.

Since the conventional apparatus described in JP-A-2002-005858 is a total reflecting type in which a sample is obliquely irradiated with primary X-rays, the X-ray source needs to be installed to depart from the position immediately above the sample and thus there is a problem in that the X-ray shielding enclosure should be increased in size in the horizontal direction for the purpose of accommodating the X-ray source.

SUMMARY

The present disclosure has been made in view of the above-described circumstances, and one of objects of the present disclosure is to provide an X-ray fluorescence analyzer and an X-ray fluorescence analyzing method that is capable to decrease a size of the apparatus and efficiently measure a large-area sample.

According to an exemplary embodiment of the present disclosure, there is provided an X-ray fluorescence analyzer including: a sample stage having a mounting surface on which a sample is mounted; an X-ray source configured to irradiate the sample with the primary X-rays and disposed immediately above an irradiation position of the sample; a detector configured to detect fluorescent X-rays emitted from the sample irradiated with the primary X-rays; an X stage configured to move the sample stage in an X direction that is parallel to the mounting surface; a Y stage configured to move the sample stage in a Y direction that is parallel to the mounting surface and perpendicular to the X direction; a θ stage configured to have a rotation center at the center of the mounting surface and to rotate the sample stage around a rotation axis perpendicular to the mounting surface; and a shielding container configured to accommodate the sample stage, the X-ray source, the detector, the X stage, the Y stage, and the θ stage. The irradiation position with the primary X-rays is set at an offset position from a movement center of the X stage and the Y stage. An irradiation area that is irradiatable with the primary X-rays is set to a selected segmented area, in which the irradiation position is disposed, from among segmented areas that are defined by segmenting the surface of the sample into four parts with a virtual segment line in the X direction and a virtual segment line in the Y direction passing through the movement center when the X stage and the Y stage are moved in a state in which the θ stage is not moved. The θ stage is configured to switch the selected segmented area as the irradiation area into any one of the segmented areas by rotating the sample stage by every 90 degrees.

According to another exemplary embodiment of the present disclosure, there is provided an X-ray fluorescence analyzing method of an X-ray fluorescence analyzer. The X-ray fluorescence analyzer is provided with: a sample stage having a mounting surface on which a sample is mounted; an X-ray source configured to irradiate the sample with the primary X-rays and disposed immediately above an irradiation position of the sample; a detector configured to detect fluorescent X-rays emitted from the sample irradiated with the primary X-rays; an X stage configured to move the sample stage in an X direction that is parallel to the mounting surface; a Y stage configured to move the sample stage in a Y direction that is parallel to the mounting surface and perpendicular to the X direction; a θ stage configured to have a rotation center at the center of the mounting surface and to rotate the sample stage around a rotation axis perpendicular to the mounting surface; and a shielding container configured to accommodate the sample stage, the X-ray source, the detector, the X stage, the Y stage, and the θ stage. The X-ray fluorescence analyzing method includes: mounting the sample on the sample stage; setting the irradiation position with the primary X-rays at an offset position from a movement center of the X stage and the Y stage; setting an irradiation area that is irradiatable with the primary X-rays to a selected segmented area, in which the irradiation position is disposed, from among segmented areas that are defined by segmenting the surface of the sample into four parts with a virtual segment line in the X direction and a virtual segment line in the Y direction passing through the movement center when the X stage and the Y stage are moved in a state in which the θ stage is not moved; and switching the selected segmented area as the irradiation area into any one of the segmented areas by rotating the sample stage by every 90 degrees with the θ stage.

BRIEF DESCRIPTION OF THE DRAWINGS

The above and other aspects of the present disclosure will become more apparent and more readily appreciated from the following description of illustrative embodiments of the present disclosure taken in conjunction with the attached drawings, in which.

DETAILED DESCRIPTION

Hereinafter, an X-ray fluorescence analyzer and an X-ray fluorescence analyzing method according to an embodiment of the present disclosure will be described with reference to FIGS. 1A to 4C.

Figure 1A:
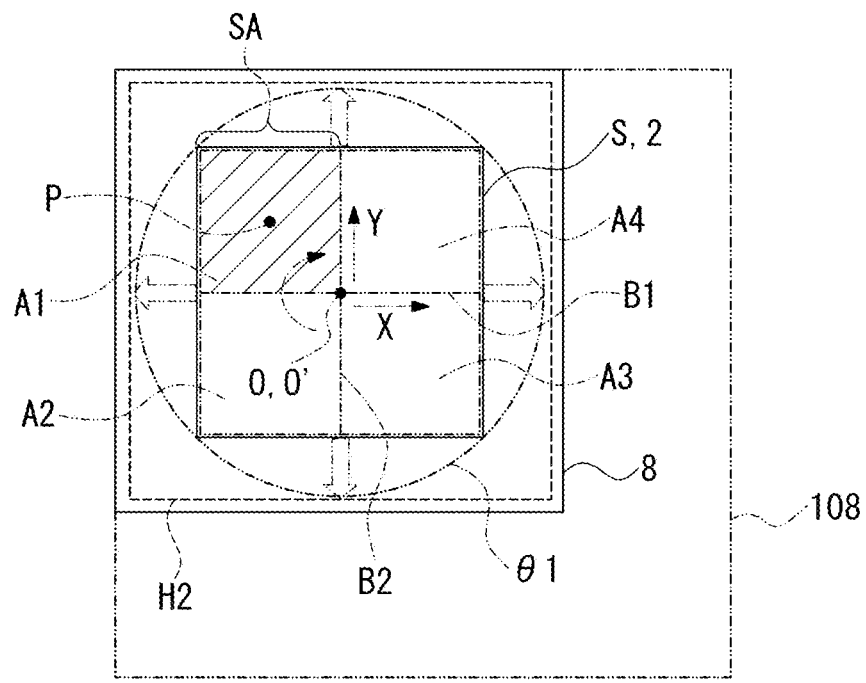
FIGS. 1A and 1B are respectively a plan view illustrating segmented areas and an irradiation area in an X-ray fluorescence analyzer and an X-ray fluorescence analyzing method according to an embodiment of the present disclosure and a diagram illustrating a positional relationship to a rotation center by slightly moving X and Y stages from a movement center.
Figure 1B:
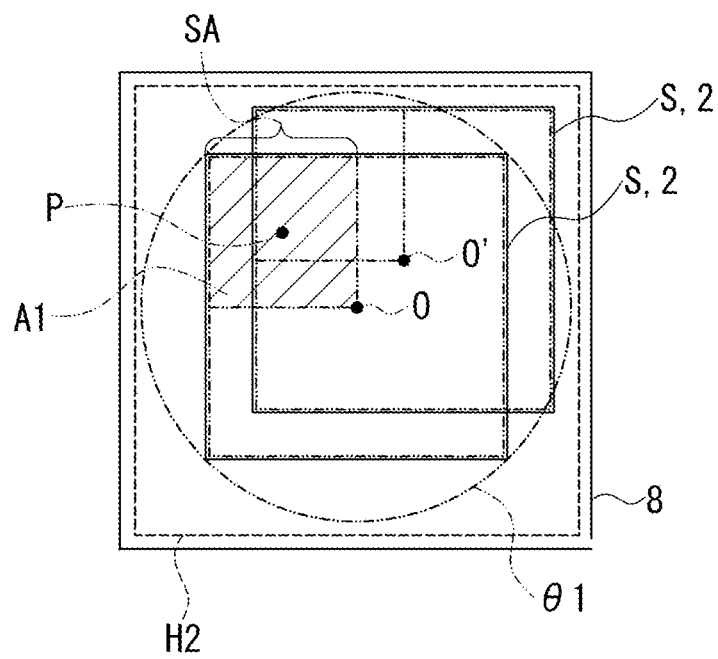
Figure 2:
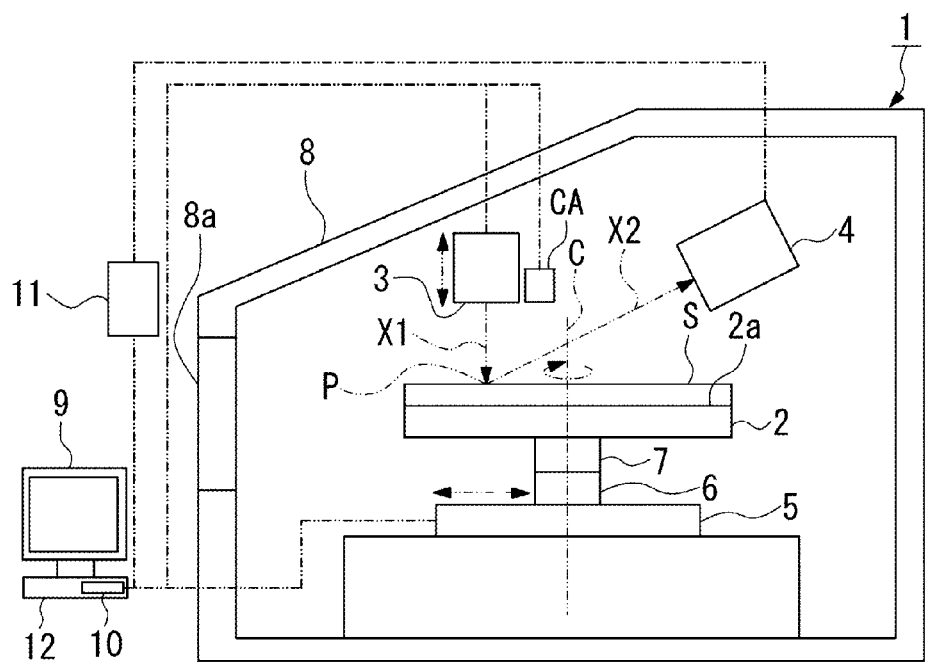
FIG. 2 is a diagram schematically illustrating a configuration of the X-ray fluorescence analyzer according to the embodiment.

As illustrated in FIGS. 1A and 1B and FIG. 2, an X-ray fluorescence analyzer 1 according to the embodiment is provided with: a sample stage 2 having a mounting surface 2a on which a sample S is set; an X-ray source 3 disposed immediately above the sample S and configured to irradiate the sample S with primary X-rays X1; a detector 4 configured to detect fluorescent X-rays X2 emitted from the sample S irradiated with the primary X-rays X1; an X stage 5 configured to move the sample stage 2 in an X direction which is one direction parallel to the mounting surface 2a; a Y stage 6 configured to move the sample stage 2 in a Y direction parallel to the mounting surface 2a and perpendicular to the X direction; a θ stage 7 configured to have a rotation center O' at the center of the mounting surface 2a and to rotate the sample stage 2 around a rotation axis C perpendicular to the mounting surface 2a; and a shielding container 8 configured to accommodate at least the sample stage 2, the X-ray source 3, the detector 4, the X stage 5, the Y stage 6, and the θ stage 7.

A movement center O which is the center of movable ranges of the X stage 5 and the Y stage 6 and the rotation center O' of the θ stage 7 match each other when the X stage 5 and the Y stage 6 are arranged at the centers of the movable ranges, respectively.

An irradiation position P with the primary X-rays X1 is set at an offset position from the movement center O.

An irradiation area SA, in which the primary X-rays X1 can be irradiated by moving the X stage 5 and the Y stage 6 without moving the θ stage 7, is set to one segmented area in which the irradiation position P is disposed out of segmented areas A1 to A4 which are obtained by segmenting the surface of the sample S into four parts using a virtual segment line B1 in the X direction and a virtual segment line B2 in the Y direction passing through the movement center O.

The θ stage 7 can switch the segmented areas A1 to A4 as the irradiation area SA by rotating the sample stage 2 by every 90 degrees.

For example, in FIGS. 1A and 1B, the segmented area A1 in which the irradiation position P is disposed is the irradiation area SA. The irradiation area SA is the movable range of the X stage 5 and the Y stage 6 in a state in which the irradiation position P is disposed in the segmented area A1 and is hatched in FIGS. 1A and 1B. The irradiation area SA is a quarter of the surface of the sample S.

As illustrated in FIGS. 1A and 1B, sign θ1 denotes a rotational orbit of corners of the sample S when the θ stage 7 is rotated in a state in which the irradiation position P is disposed at the center of the irradiation area SA. The movable range when the θ stage 7, the X stage 5, and the Y stage 6 are moved is denoted by sign H2 in FIGS. 1A and 1B.

The X-ray fluorescence analyzer 1 is provided with an imaging unit CA that captures an image of the segmented areas A1 to A4 as the irradiation area SA, a display unit 9 that displays the image captured by the imaging unit CA, and an image processing unit 10 that arranges the images of four segmented areas A1 to A4, which are captured by the imaging unit CA while switching the θ stage 7, on the display unit 9 to display a combined image of the entire surface of the sample S.

The X-ray fluorescence analyzer 1 is also provided with an analyzer 11 that is connected to the detector 4 so as to analyze a signal from the detector 4 and a control unit 12 that is connected to the X-ray source 3, the detector 4, the X stage 5, the Y stage 6, the θ stage 7, the imaging unit CA, the display unit 9, and the analyzer 11 so as to control the elements.

In order to visually check the irradiation position P, a guide light irradiation mechanism (not illustrated) that irradiates the irradiation position P or the periphery thereof with visible guide light is disposed above the sample stage 2.

The X-ray source 3 is supported by a Z stage (not illustrated) that is movable in a Z direction (up-down direction) perpendicular to the X direction and the Y direction.

The θ stage 7 may be rotated manually, but the sample stage 2 may be rotated automatically by every 90 degrees under the control of the control unit 12.

The θ stage 7 is installed on the X stage 5 and the Y stage 6. Accordingly, it is possible to reduce a burden of weight of the θ stage 7.

The sample S has, for example, a square shape and an example thereof is an electronic printed circuit board. The sample stage 2 and the sample S are set to the same size (or the sample stage 2 is set to be larger than the sample S).

Figure 3:
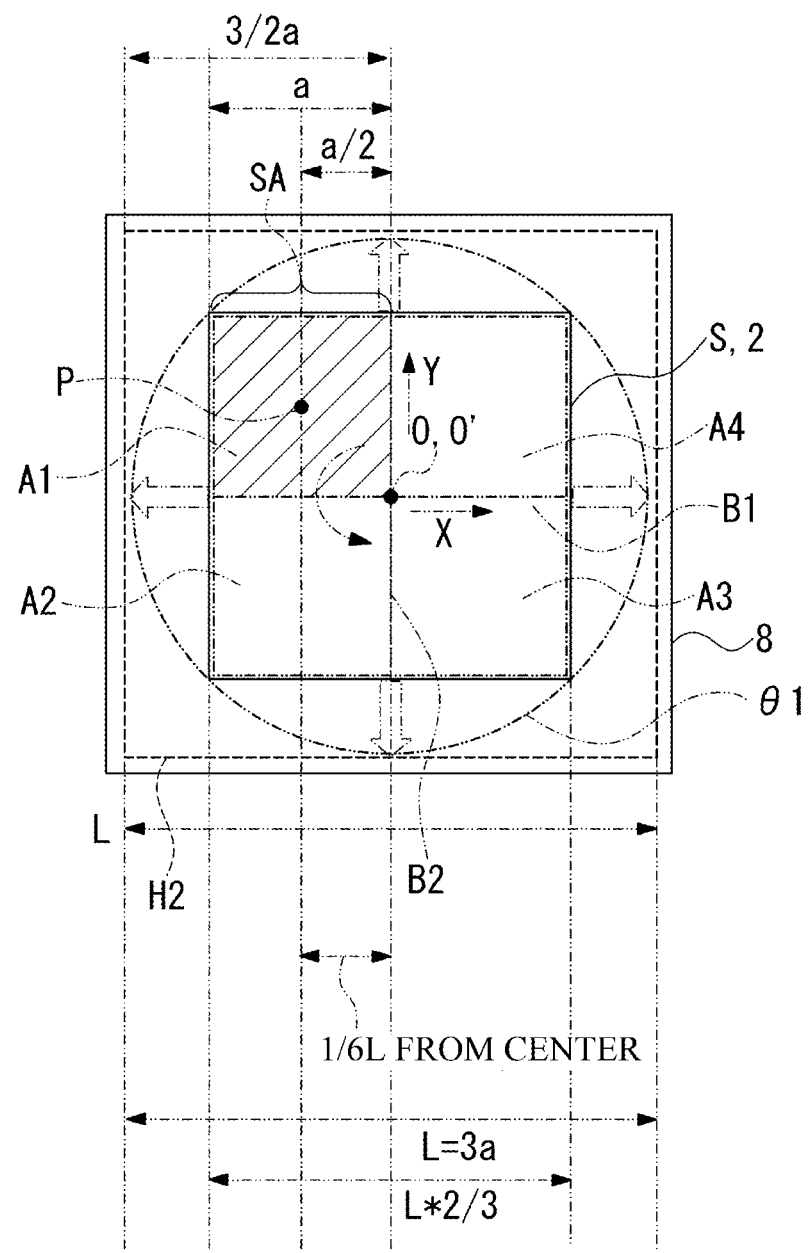
FIG. 3 is a diagram illustrating a dimensional relationship among a sample, the segmented areas, the irradiation area, and movable range lengths of the stages according to the embodiment.

Regarding the dimensional relationship between the sample S and the movable range of the X stage 5 and the Y stage 6 in the embodiment, as illustrated in FIG. 3, when half a length of one side of the sample S is defined as "a" and the movable range length of the X stage 5 and the Y stage 6 is defined as L, the movable range length L is set to "3×a". At this time, one side (having a length of "2×a") of the sample S is "(2/3)×L".

The movement center O of the X stage 5 and the Y stage 6 matches the rotation center O' in a state in which the X stage and the Y stage are not moved from the center of the movable range, and the irradiation position P is set to a position separated by "−(1/6)×L" in the X direction and by "+(1/6)×L" in the Y direction from the movement center O of the X stage 5 and the Y stage 6.

As illustrated in FIG. 3, when it is assumed that the irradiation position P is set to the center of the segmented area A1 as the irradiation area SA, the entire segmented area A1 can be measured by moving the X stage 5 or the Y stage 6 by a distance of "(3/2)×a" in the X direction or the Y direction. The segmented area A1 is a quarter of the surface of the sample S and the other segmented areas A2 to A4 can be measured by rotating the sample S by every 90 degrees.

The center of the irradiation area SA is set to a position which is shifted by "a/2" in the X direction and the Y direction from the movement center O of the sample stage 2 and this position is the irradiation position P.

The shielding container 8 is provided with an input and output port 8a of the sample S and the input and output port 8a is installed on the side surface of the shielding container 8 closest to the irradiation position P.

The shielding container 8 is an X-ray shielding enclosure and is formed of an iron plate or the like.

The length of one side of an inner surface in the X-Y direction of the shielding container 8 is at least 1.5 times ("3×a") of the length ("2×a") of one side of the sample stage 2.

In order to compare the occupied area of the shielding container 8 in the embodiment with the occupied area of the X-ray shielding enclosure 108 in the apparatus including only the X stage and the Y stage in the related art, the size of the X-ray shielding enclosure 108 in the related art is denoted by a two-dot chained line in FIG. 1A.

The image processing unit 10 has a function of rotating the images of the four segmented areas A1 to A4 in reverse direction by the same degree of rotation as the rotation of the θ stage 7 when each image corresponding to the irradiation area SA and forming a combined image.

The X-ray source 3 is disposed immediately above the irradiation position P and the detector 4 is disposed obliquely above the irradiation position P.

The imaging unit CA is an observation camera on which a CCD or the like is mounted and is installed above the sample stage 2 so as to image the sample S on the sample stage 2.

The X-ray source 3 is an X-ray tube capable of emitting primary X-rays X1 and serves to emit X-rays, which are generated by accelerating thermoelectrons generated from a filament (cathode) in the tube by a voltage applied between the filament (cathode) and a target (anode) and causing the thermoelectrons to collide with tungsten (W), molybdenum (Mo), chromium (Cr), or the like as the target, as the primary X-rays X1 from a window formed of a beryllium foil or the like.

The detector 4 is provided with a semiconductor detection device (for example, a silicon (Si) device which is a pin-structure diode) (not illustrated) and serves to generate a current pulse corresponding to one X-ray photon when the one X-ray photon is incident. The instantaneous current value of the current pulse is in proportion to energy of incident characteristic X-rays. The detector 4 is set to convert the current pulse generated from the semiconductor detection device into a voltage pulse, to amplify the voltage pulse, and to output the voltage pulse as a signal.

The analyzer 11 may be a pulse height analyzer (multi-channel analyzer) that acquires a height of a voltage pulse from the signal and generates an energy spectrum.

The control unit 12 is a computer including a processor (CPU) and the like, has the image processing unit 10 therein, and has a function of displaying an analysis result on the display unit 9.

An X-ray fluorescence analyzing method using the X-ray fluorescence analyzer 1 according to the embodiment will be described below.

First, the input and output port 8a is opened and a sample S is mounted in a range included in the sample stage 2 along guide light. After the sample S is mounted, the input and output port 8a is closed and a fluorescent X-ray analysis is performed.

In performing the fluorescent X-ray analysis, the irradiation position P of primary X-rays X1 is set to depart from the movement center O. At this time, as illustrated in FIGS. 1A and 1B, for example, the irradiation position P is set in the segmented area A1 among four segmented areas A1 to A4. The irradiation area SA which can be irradiated with the primary X-rays X1 when the X stage 5 and the Y stage 6 are moved in a state in which the θ stage 7 is not moved is set to one (segment area A1) in which the irradiation position is located among the four segmented areas A1 to A4.

In this state, only the X stage 5 and the Y stage 6 are moved to position the irradiation position P in the segmented area A1 as the irradiation area SA at a measurement point, fluorescent X-rays X2 generated by irradiating the measurement point with the primary X-rays X1 are detected by the detector 4, and the fluorescent X-ray analysis in the segmented area A1 is performed. At this time, the segmented area A1 is imaged by the imaging unit CA.

Then, the X stage 5 and the Y stage 6 are returned to the movement center O to match the movement center O with the rotation center O', the sample stage 2 is rotated (for example, rotated to the right side) by 90 degrees to switch the segmented area as the irradiation area SA from the segmented area A1 to the segmented area A2 by the θ stage 7, and measurement is performed in the same way as described above.

Subsequently, the X stage 5 and the Y stage 6 are returned to the movement center O again, the sample stage 2 is additionally rotated by 90 degrees to the right side to switch the segmented area as the irradiation area SA from the segmented area A2 to the segmented area A3 by the θ stage 7, and measurement is performed. Finally, the X stage 5 and the Y stage 6 are returned to the movement center O, the sample stage 2 is additionally rotated by 90 degrees to the right side to switch the segmented area as the irradiation area SA from the segmented area A3 to the segmented area A4 by the θ stage 7, and measurement is performed. In this way, by rotating the sample stage 2 by every 90 degrees using the θ stage 7 to sequentially switch the irradiation area SA to the segmented areas A1 to A4 and performing the measurement, measurement for the fluorescent X-ray analysis is performed on the entire surface (all the four segmented areas) of the sample S.

Figure 4A:
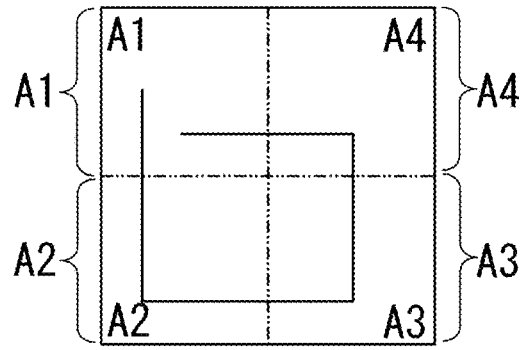
FIGS. 4A, 4B, and 4C are diagrams illustrating a method of displaying a combined image formed by an image processing unit according to the embodiment.
Figure 4B:
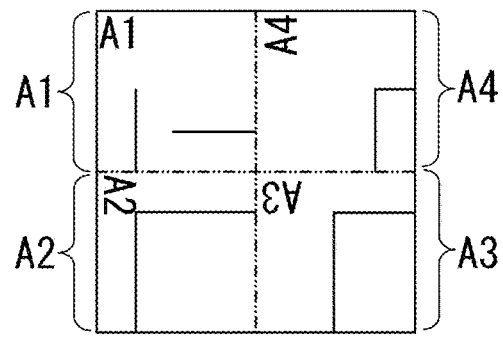
Figure 4C:
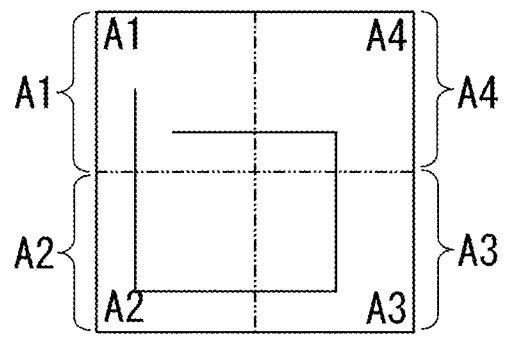
Figure 5:
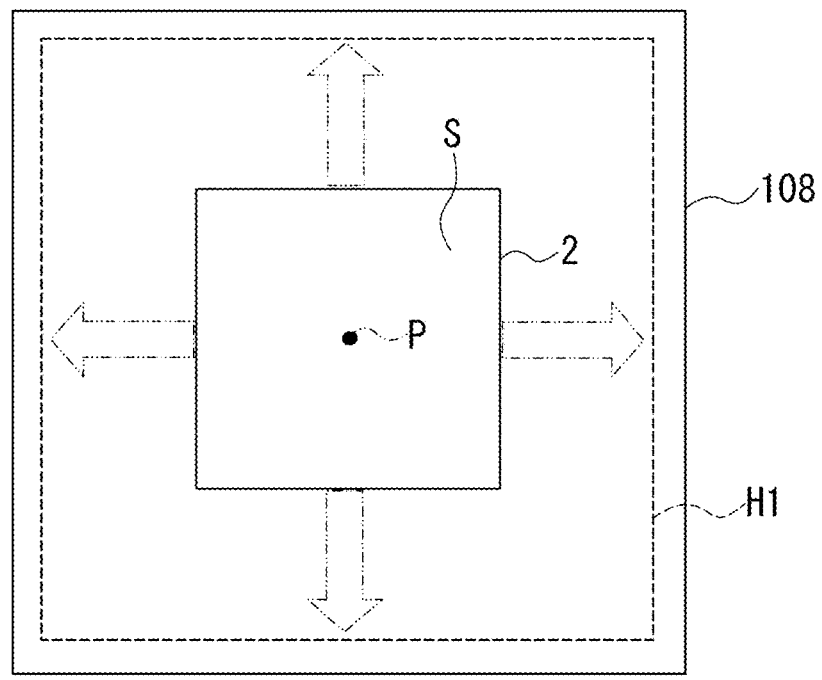
FIG. 5 is a plan view illustrating a positional relationship among a sample, movable ranges of stages, and an X-ray shielding enclosure in an X-ray fluorescence analyzer and an X-ray fluorescence analyzing method according to the related art.

The image processing unit 10 arranges the images of the four segmented areas A1 to A4 captured by the imaging unit CA on the display unit 9 at time of the switching using the θ stage 7 and displays a combined image of the entire surface of the sample S on the display unit 9. However, when the sample S is segmented into four segmented areas A1 to A4 and the images of the segmented areas A1 to A4 captured in a state in which the sample is rotated are arranged and displayed at the same positions as illustrated in FIG. 4A, the segmented areas A2 to A4 other than the non-rotated segmented area A1 do not have correct image directions as illustrated in FIG. 4B. In FIGS. 4A to 4C, the signs of the segmented areas corresponding to the images and lines extending over the segmented areas are illustrated to easily understand the image directions.

The image processing unit 10 rotates the images of the four segmented areas A1 to A4 in reverse direction by the same degree of rotation as the rotation of the θ stage 7 when the corresponding image becomes the irradiation area SA so as to return the image directions to the initial states and forms a combined image.

As illustrated in FIG. 4C, the image of the non rotated segmented area A1 is captured when the sample S is not rotated, the image of the segmented area A2 when the sample S is rotated to the right side by 90 degrees is rotated to the left side by 90 degrees, the image of the segmented area A3 when the sample S is rotated to the right side by 180 degrees is rotated to the left side by 180 degrees, the image of the segmented area A4 when the sample S is rotated to the right side by 270 degrees is rotated to the left side by 270 degrees, and the images are arranged at the corresponding positions to form a combined image. The combined image is displayed on the display unit 9.

In this way, in the X-ray fluorescence analyzer 1 according to the embodiment, the irradiation area SA capable of being irradiated with the primary X-rays X1 when the X stage 5 and the Y stage 6 are moved in a state in which the θ stage 7 is not moved is set to one in which the irradiation position P is disposed among the segmented areas A1 to A4 which are obtained by segmenting the surface of the sample S into four parts using the virtual segment line B1 in the X direction and the virtual segment line B2 in the Y direction passing through the rotation center O', and the θ stage 7 can rotate the sample stage 2 by every 90 degrees to switch the irradiation area SA to the segmented areas A1 to A4. Accordingly, it is possible to both decrease the size of the entire apparatus and efficiently measure a sample. By rotating the sample stage 2 by every 90 degrees to sequentially irradiate the area SA of the segmented areas A1 to A4 and performing the measurement, it is possible to efficiently measure the entire surface of a large-area sample using even small stages having a small movable range.

In performing the fluorescent X-ray analysis, all the images of four segmented areas A1 to A4 can be acquired and the measurement point can be designated on the sample image displayed on the display unit 9 based on the combined image formed by the image processing unit 10 or the measurement can be performed depending on the coordinates on the sample stage.

By setting the dimensional and positional relationships between the irradiation area SA and the irradiation position P as described above, it is possible to efficiently measure the entire surface of the sample to correspond to the decreased movable ranges of the X stage 5 and the Y stage 6 suitable for a square sample S.

Since the input and output port 8a is formed on the side surface of the shielding container 8 closest to the irradiation position P, it is easy to input and output the sample S and to position the sample. Since the shielding container 8 is air-tight and closed by closing the input and output port 8a, it is possible to prevent or suppress exposure of an operator during the fluorescent X-ray analysis.

Since the image processing unit 10 rotates the images of four segmented areas A1 to A4 in reverse directionby the same degree of rotation as the rotation of the θ stage 7 when the images are set as the irradiation area SA and forms a combined image, it is possible to display the entire surface of the sample stage 2 in the normal direction before the rotation by returning the images captured through rotation at the time of measurement to the original directions and arranging and combining the images.

Accordingly, an operator can refer to the coordinates corresponding to the combined image and thus can easily determine a measurement point on the actual sample stage 2 based on the relationship between the coordinates of the measurement point designated on the combined image and the coordinates on the actual sample stage 2 at the time of measurement.

In the X-ray fluorescence analyzer 1 according to the embodiment, the length of one side of an inner surface in the X direction and the Y direction (X-Y directions) of the shielding container accommodating the sample stage is at least 1.5 times the length of one side of the sample stage.

In the X-ray fluorescence analyzer 1, since four segmented areas as an irradiation area are sequentially switched and measured by rotating the sample stage by every 90 degrees, the entire surface of one corresponding area can be efficiently measured with the same degree of movement as in the X-Y directions of the area. Accordingly, the shielding container preferably has a minimum inner wall gap of the same size so as to enable movement in a range which is 1.5 times the size of the sample stage.

According to the present disclosure, the following advantages can be obtained. According to the X-ray fluorescence analyzer 1 and the X-ray fluorescence analyzing method of the present disclosure, since the θ stage can switch a segmented area as an irradiation area by rotating the sample stage by every 90 degrees, it is possible to achieve both a decrease in the size of the apparatus as a whole and carry-out efficient measurement of a sample. Accordingly, it is possible to efficiently measure the entire surface of a large-area sample with a small stage area as well as decrease the size of the apparatus reducing the cost of the apparatus.

The present disclosure is not limited to the specific example as described in the above with respect to the embodiment, and the X-ray fluorescence analyzer and the X-ray fluorescence analyzing method may be modified in various forms without departing from the spirit and scope of the present disclosure.

For example, in the above-described embodiment, an energy-dispersion type X-ray fluorescence analyzer is described, which measures energy and intensity of X-rays using a pulse height analyzer. However, a wavelength-dispersion type X-ray fluorescence analyzer may also be employed, which disperses fluorescent X-rays using a dispersive crystal and measures a wavelength and intensity of the X-rays.

The input and output port 8a of the sample S of the shielding container 8 may be formed on a side surface separated apart from the irradiation position P. In this case, it is possible to take a large input and output port and thus to easily position the sample S.

What is claimed is:

1. An X-ray fluorescence analyzer comprising:
   a sample stage having a mounting surface on which a sample is mounted;
   an X-ray source configured to irradiate the sample with the primary X-rays and disposed immediately above an irradiation position of the sample;
   a detector configured to detect fluorescent X-rays emitted from the sample irradiated with the primary X-rays;
   an X stage configured to move the sample stage in an X direction that is parallel to the mounting surface;
   a Y stage configured to move the sample stage in a Y direction that is parallel to the mounting surface and perpendicular to the X direction;
   a θ stage configured to have a rotation center at the center of the mounting surface and to rotate the sample stage around a rotation axis perpendicular to the mounting surface; and
   a shielding container configured to accommodate the sample stage, the X-ray source, the detector, the X stage, the Y stage, and the θ stage,
   wherein the irradiation position with the primary X-rays is set at an offset position from a movement center of the X stage and the Y stage,
   wherein an irradiation area that is irradiatable with the primary X-rays is set to a selected segmented area, in which the irradiation position is disposed, from among segmented areas that are defined by segmenting the surface of the sample into four parts with a virtual segment line in the X direction and a virtual segment line in the Y direction passing through the movement center when the X stage and the Y stage are moved in a state in which the θ stage is not moved, and
   wherein the θ stage is configured to switch the selected segmented area as the irradiation area into any one of the segmented areas by rotating the sample stage by every 90 degrees.

2. The X-ray fluorescence analyzer according to claim 1,
   wherein the sample stage has a square shape,
   wherein when half a length of one side of the sample stage is defined as "a" and a movable range length of the X stage and the Y stage is defined as L, the movable range length L is set to "3×a",
   wherein the movement center of the X stage and the Y stage is set to match the rotation center, and
   wherein the irradiation position is set to a position at "−(1/6)×L" shifted in the X direction and "+(1/6)×L" shifted in the Y direction from the movement center of the X stage and the Y stage.

3. The X-ray fluorescence analyzer according to claim 1,
   wherein the shielding container is provided with an input and output port of the sample, the input and output port being provided on a side surface closest to the irradiation position of the shielding container.

4. The X-ray fluorescence analyzer according to claim 1 further comprising:
   an imaging unit configured to capture an image of the segmented area selected as the irradiation area;
   a display unit configured to display the image captured by the imaging unit; and
   an image processing unit configured to arrange images of the four segmented areas captured by the imaging unit while the four segmented areas are switched by the θ stage, and generate a combined image of an entire surface of the sample stage to be displayed on the display unit,
   wherein the image processing unit generates the combined image by rotating the images of the four segmented areas in a reverse direction by the same degree of rotation as the rotation of the θ stage when each of the images of the four segmented areas is set as the irradiation area.

5. The X-ray fluorescence analyzer according to claim 1,
   wherein the length of one side of an inner surface in the X direction and the Y direction of the shielding container accommodating the sample stage is at least 1.5 times the length of one side of the sample stage.

6. An X-ray fluorescence analyzing method of an X-ray fluorescence analyzer,
   wherein the X-ray fluorescence analyzer is provided with:
   a sample stage having a mounting surface on which a sample is mounted;
   an X-ray source configured to irradiate the sample with the primary X-rays and disposed immediately above an irradiation position of the sample;
   a detector configured to detect fluorescent X-rays emitted from the sample irradiated with the primary X-rays;
   an X stage configured to move the sample stage in an X direction that is parallel to the mounting surface;
   a Y stage configured to move the sample stage in a Y direction that is parallel to the mounting surface and perpendicular to the X direction;

a θ stage configured to have a rotation center at the center of the mounting surface and to rotate the sample stage around a rotation axis perpendicular to the mounting surface; and a shielding container configured to accommodate the sample stage, the X-ray source, the detector, the X stage, the Y stage, and the θ stage, wherein the X-ray fluorescence analyzing method comprises:

mounting the sample on the sample stage;

setting the irradiation position with the primary X-rays at an offset position from a movement center of the X stage and the Y stage;

setting an irradiation area that is irradiatable with the primary X-rays to a selected segmented area, in which the irradiation position is disposed, from among segmented areas that are defined by segmenting the surface of the sample into four parts with a virtual segment line in the X direction and a virtual segment line in the Y direction passing through the movement center when the X stage and the Y stage are moved in a state in which the θ stage is not moved; and switching the selected segmented area as the irradiation area into any one of the segmented areas by rotating the sample stage by every 90 degrees with the θ stage.

7. The X-ray fluorescence analyzing method according to claim 6, wherein the sample stage has a square shape, wherein the X-ray fluorescence analyzing method further comprises:

setting a movable range length L to "3×a", wherein half a length of one side of the sample stage is defined as "a" and a movable range length of the X stage and the Y stage is defined as L;

setting the movement center of the X stage and the Y stage to match the rotation center; and setting the irradiation position to a position at "−(1/6)×L" shifted in the X direction and "+(1/6)×L" shifted in the Y direction from the movement center of the X stage and the Y stage.

8. The X-ray fluorescence analyzing method according to claim 6, wherein the X-ray fluorescence analyzer is further provided with:

an imaging unit configured to capture an image of the segmented area selected as the irradiation area; and a display unit configured to display the image captured by the imaging unit, and wherein the X-ray fluorescence analyzing method further comprises:

arranging images of the four segmented areas captured by the imaging unit while the four segmented areas are switched by the θ stage to generate a combined image of an entire surface of the sample stage to be displayed on the display unit; and generating the combined image by rotating the images of the four segmented areas in a reverse direction by the same degree of rotation as the rotation of the θ stage when each of the images of the four segmented areas is set as the irradiation area.

* * * * *